United States Patent
Yoon et al.

(10) Patent No.: US 9,429,333 B2
(45) Date of Patent: Aug. 30, 2016

(54) HUMIDIFIER

(71) Applicant: SAMSUNG ELECTRONICS CO., LTD., Suwon-si (KR)

(72) Inventors: Jin Kook Yoon, Hwaseong-si (KR); Young Chul Ko, Suwon-si (KR); Daeun Kim, Seoul (KR); Jee Yeon Kim, Yongin-si (KR)

(73) Assignee: SAMSUNG ELECTRONICS CO., LTD., Suwon-Si (KR)

( * ) Notice: Subject to any disclaimer, the term of this patent is extended or adjusted under 35 U.S.C. 154(b) by 361 days.

(21) Appl. No.: 13/743,719

(22) Filed: Jan. 17, 2013

(65) Prior Publication Data

US 2013/0186748 A1    Jul. 25, 2013

(30) Foreign Application Priority Data

Jan. 19, 2012   (KR) .................. 10-2012-0005989

(51) Int. Cl.
| | |
|---|---|
| A61L 2/18 | (2006.01) |
| A61L 9/14 | (2006.01) |
| F24F 6/12 | (2006.01) |
| C02F 1/467 | (2006.01) |
| B05B 17/06 | (2006.01) |

(52) U.S. Cl.
CPC .. F24F 6/12 (2013.01); A61L 2/18 (2013.01); A61L 9/14 (2013.01); C02F 1/467 (2013.01); *A61L 2202/11* (2013.01); *A61L 2209/213* (2013.01); *B05B 17/0615* (2013.01); *F24F 2221/225* (2013.01)

(58) Field of Classification Search
None
See application file for complete search history.

(56) References Cited

U.S. PATENT DOCUMENTS

| | | | | |
|---|---|---|---|---|
| 4,663,091 | A | * | 5/1987 | Seo .............................. 261/72.1 |
| 5,014,338 | A | * | 5/1991 | Glucksman ............. F24F 6/025 |
| | | | | 200/81.9 R |
| 5,199,276 | A | * | 4/1993 | Sullivan ......................... 62/291 |
| 5,256,268 | A | * | 10/1993 | Goto et al. ..................... 204/268 |
| 5,520,854 | A | * | 5/1996 | Porco et al. ...................... 261/5 |
| 6,053,482 | A | * | 4/2000 | Glenn et al. ...................... 261/4 |
| 2004/0022675 | A1 | * | 2/2004 | An .................................. 422/29 |
| 2004/0045909 | A1 | * | 3/2004 | Tomioka et al. ............. 210/748 |
| 2005/0000243 | A1 | * | 1/2005 | Hwang et al. .................. 62/317 |
| 2005/0155939 | A1 | * | 7/2005 | Stadelmann ................. 210/764 |
| 2006/0273470 | A1 | * | 12/2006 | Takahashi et al. ............... 261/4 |
| 2010/0200398 | A1 | * | 8/2010 | Thiruppathi et al. ......... 204/274 |
| 2011/0100838 | A1 | * | 5/2011 | Kim et al. ..................... 205/742 |
| 2012/0071081 | A1 | * | 3/2012 | Park et al. ..................... 454/252 |

FOREIGN PATENT DOCUMENTS

WO    WO 2010/137867 A2 * 12/2010 ............... F24F 6/10

* cited by examiner

*Primary Examiner* — Harry D Wilkins, III
(74) *Attorney, Agent, or Firm* — Staas & Halsey LLP

(57) ABSTRACT

A humidifier including a storage chamber configured to store water, an electrolytic unit configured to electrolyze water, a first and second pipe to which the electrolyzed water is introduced, a first and second valve configured to open/close a fluid path of the first pipe and second pipe, a filter unit disposed at the first pipe and configured to filter the electrolyzed water, a humidification chamber configured to be supplied with water from one of the first or the second pipe, and a control unit configured to supply the filtered water to the humidification chamber at a humidification mode by controlling the first valve and supply the electrolyzed water to the humidification chamber at a sterilization mode by controlling the second valve, the humidifier further including a drainage hole and a drainage valve to open/close the drainage hole, and a tray to store the water being discharged through the drainage hole.

24 Claims, 10 Drawing Sheets

HUMIDIFIER

CROSS-REFERENCE TO RELATED APPLICATIONS

This application claims the priority benefit of Korean Patent Application No. 10-2012-0005989, filed on Jan. 19, 2012 in the Korean Intellectual Property Office, the disclosure of which is incorporated herein by reference.

BACKGROUND

1. Field

Embodiments of the present disclosure relate to a humidifier configured to prevent a proliferation of a microorganism.

2. Description of the Related Art

A humidifier is an apparatus configured to increase or maintain humidity in air at an indoor space, and is capable of atomizing or vaporizing water by use of electricity before spraying the atomized or vaporized water to an outside.

Types of a humidifier may include a heating type, an ultrasonic type, a combination type having the heating type and the ultrasonic type integrated, a centrifugal spraying type configured to split water into small particles by having the water collide onto a screen using a centrifugal force before releasing such to an outside, and a filter evaporating type configured to generate moisture by evaporating water by having air pass through a wet filter.

As an interest toward hygiene grows along with technological advancement and economic growth, sanitary matters concerning a humidifier is raised. Particularly, as a controversy grows over use of conventional sterilization chemical containing hazardous substance, matters related to sterilizing a humidifier are further widened.

Since a humidifier is configured to contain water even when such is not in use, and thus, a contamination may occur caused by a proliferation of a microorganism. In addition, displeasure from a deposit formed on an exterior of a humidifier along with an odor caused by the deposit may develop.

Particularly, in a case of an ultrasonic humidifier, germs may be spread into air along with the water when the water is being sprayed.

SUMMARY

Therefore, it is an aspect of the present disclosure to provide a humidifier configured to filter and spray electrolyzed water and to perform sterilization using electrolyzed water.

It is another aspect of the present disclosure to provide a humidifier configured to discharge the remaining water after being used for a humidification in a case when a humidification mode is canceled.

It is another aspect of the present disclosure to provide a humidifier configured to change the component of water being supplied to a humidification chamber by selectively controlling in the opening of a plurality of valves disposed between a humidification chamber and a storage chamber according to a humidification mode and a sterilization mode.

Additional aspects of the disclosure will be set forth in part in the description which follows and, in part, will be apparent from the description, or may be learned by practice of the disclosure.

In accordance with one aspect of the present disclosure, a humidifier includes a storage chamber, an electrolytic unit, a first pipe and a second pipe, a first valve, a first valve, a second valve, a filter unit, a humidification chamber and a control unit. The storage chamber may be configured to store water. The electrolytic unit may be configured to electrolyze water at the storage chamber. The first pipe and the second pipe may allow the electrolyzed water to be introduced thereto. The first valve may be configured to open/close a fluid path of the first pipe. The second valve may be configured to open/close a fluid path of the second pipe. The filter unit may be disposed at the first pipe and configured to filter the electrolyzed water. The humidification chamber may be configured to be supplied with water from one of the first pipe or the second pipe. The control unit may be configured to supply the filtered water to the humidification chamber at a humidification mode by controlling the first valve, and to supply the electrolyzed water to the humidification chamber at a sterilization mode by controlling the second valve.

The humidification chamber may include a drainage hole, a drainage valve and a spray unit. The drainage hole may be configured to discharge water. The drainage valve may be configured to open/close the drainage hole. The spray unit may be configured to spray the filtered water at the humidification mode.

The humidifier may further include a tray. The tray may be installed at the humidification chamber and configured to store the water discharged through the drainage hole of the humidification chamber.

The humidifier may further include a drainage pipe. The drainage pipe may be connected to the drainage hole and configured to discharge the water of the humidification chamber to be discharged to an outside.

The control unit may be configured to supply the electrolyzed water to the humidification chamber through the second pipe by controlling the second valve at ON position when the humidification mode is cancelled.

The control unit may be configured to discharge a remaining of the filtered water that remains after being used for a humidification, by controlling the drainage valve at ON position when the humidification mode is cancelled.

The control unit may be configured to discharge the electrolyzed water to the tray by controlling the drainage valve at ON position when the sterilization mode is cancelled.

The electrolytic unit may be disposed at an inside the storage chamber.

The electrolytic unit may include a first electrode and a second electrode.

The electrolytic unit may include a first electrolytic chamber having the first electrode disposed thereon, a second electrolytic chamber having the second electrode disposed thereon, and an exchange membrane disposed between the first electrolytic chamber and the second electrolytic chamber, the electrolytic unit configured to discharge reduced water between the reduced water and sterilization water that are generated at the first electrolytic chamber and the second electrolytic chamber to the outside while supplying the sterilization water to the storage chamber.

The humidifier may further include a water tank configured to supply water to the storage chamber. The electrolytic unit may be configured to electrolyze water supplied from the water tank and to deliver the electrolyzed water to the storage chamber.

The electrolytic unit may further include a third pipe and a fourth pipe. The third pipe may be connected to the water tank. The fourth pipe may be configured to guide the sterilization water to the storage chamber.

The filter unit may include one of activated carbon and Zeolite.

The filter unit may be provided in a form of a standing shape, a block shape, or a fabric shape.

In accordance with another aspect of the present disclosure, a humidifier includes a humidification chamber, a control unit and a tray. The humidification chamber may have a spray unit, a drainage hole and a drainage valve. The spray unit may be configured to spray water. The drainage hole may be configured to discharge water. The drainage valve may be configured to open/close the drainage hole. The control unit may be configured to control an operation of the spray unit at a humidification mode and to control the drainage valve at ON position upon cancelling of the humidification mode. The tray may be installed at the humidification chamber and configured to store the water discharged through the drainage hole of the humidification chamber.

The humidifier may further include a storage chamber, an electrolytic unit, a first pipe, a filter unit, and a first valve. The storage chamber may be configured to supply water to the humidification chamber. The electrolytic unit may be configured to electrolyze the water of the storage chamber. The first pipe may be connected between the humidification chamber and the storage chamber. The filter unit may be provided at the first pipe to filter the electrolyzed water. The first valve may be provided at the first pipe and configured to control a supply of the filtered water by opening/closing the first pipe.

The control unit may be configured to control the first valve at ON position when the humidification mode is selected, and to control the drainage valve at ON position when the humidification mode is cancelled.

The control unit may be configured to control the drainage valve at ON position when a first predetermined period of time elapses after the humidification mode is cancelled.

The humidifier may further include a second pipe and a second valve. The second pipe may be disposed between the humidification chamber and the storage chamber. The second valve may be provided at the second pipe and configured to control a supply of the electrolyzed water by opening/closing a fluid path of the second pipe.

The control unit may be configured to control the drainage valve at OFF position when a second predetermined period of time elapses after the humidification mode is cancelled, and to supply the electrolyzed water to the humidification chamber through the second pipe by controlling the second valve at ON position.

The control unit may be configured to control the second valve at OFF position when a third predetermined period of time elapses after the second valve is at ON position, and to control an execution of the sterilization mode during a predetermined period of sterilization time.

The control unit may be configured to open the drainage hole by controlling the drainage valve at ON position when the sterilization time elapses.

The control unit may be configured to supply the electrolyzed water to the humidification chamber through the second pipe by controlling the second valve at ON position when the sterilization mode is selected, and to control an execution of the sterilization mode during a predetermined period of sterilization time by controlling the second valve at OFF position when a third predetermined period of time elapses after the second valve is at ON position.

The control unit may be configured to open the drainage hole by controlling the drainage valve at ON position when the sterilization time elapses.

The electrolytic unit may include a first electrolytic chamber, a second electrolytic chamber and an exchange membrane. The first electrolytic chamber may have a first electrode disposed thereon. The second electrolytic chamber may have a second electrode disposed thereon. The exchange membrane may be disposed between the first electrolytic chamber and the second electrolytic chamber. The electrolytic unit may be configured to supply water containing hypochlorous acid generated from one of the first electrolytic chamber and the second electrolytic chamber to the storage chamber.

The electrolytic unit may include a first electrode and a second electrode, and the first electrode and the second electrode may be positioned at an inside the storage chamber.

The humidifier may further include a power supply unit. The power supply unit may be configured to apply a voltage to the first electrode and the second electrode provided at the electrolytic unit at the humidification mode and the sterilization mode.

The drainage valve may be operated manually.

As described above, the humidifier has an improved sterilization capability, becoming a sterilizing humidifier for a household use and a hospital use, and may be applied to an air conditioning apparatus such as an air purifier, an air conditioner, and a thermo-hydrostatic chamber.

In addition, when the humidifier is applied to a nebulizer for treating bronchial respiratory organ as a high value-added medical apparatus, convenience as well as safety may be improved.

BRIEF DESCRIPTION OF THE DRAWINGS

These and/or other aspects of the disclosure will become apparent and more readily appreciated from the following description of embodiments, taken in conjunction with the accompanying drawings of which.

DETAILED DESCRIPTION

Figure 1:
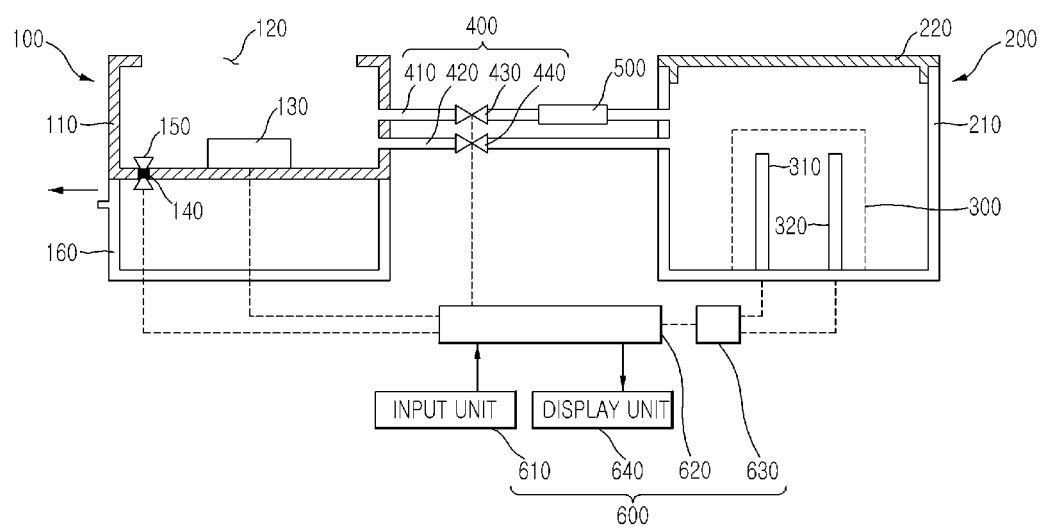
FIG. 1 is a view illustrating a humidifier in accordance with an embodiment of the present disclosure.

Reference will now be made in detail to embodiments of the present disclosure, examples of which are illustrated in the accompanying drawings, wherein like reference numerals refer to like components throughout.

Figure 2:
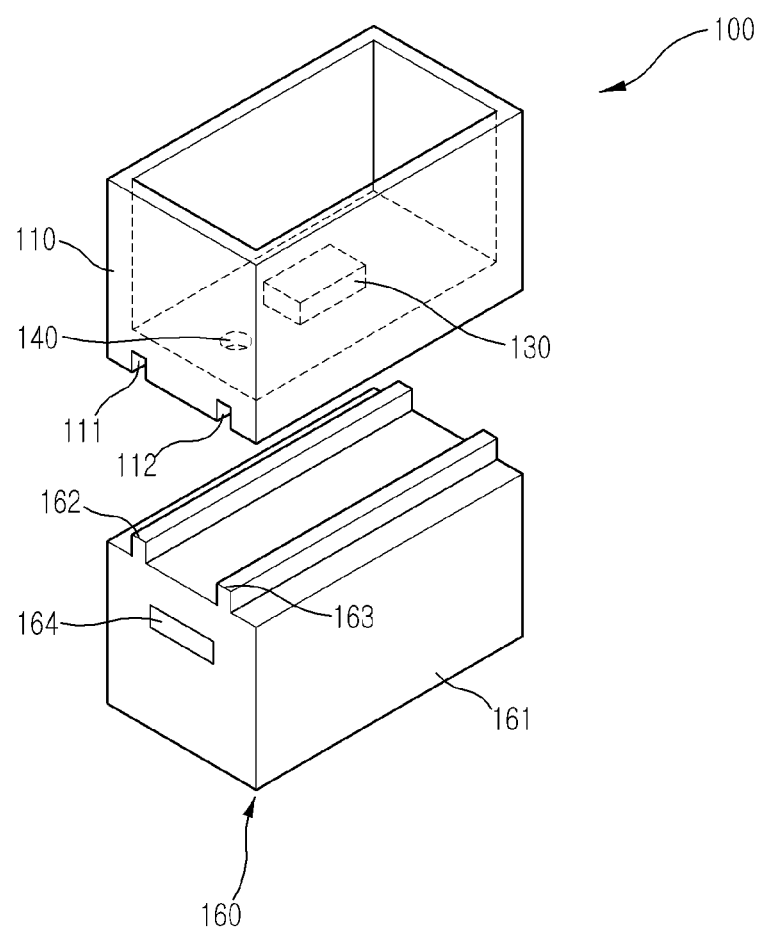
FIG. 2 is a disassembled view illustrating a humidification chamber and a tray provided at a humidifier in accordance with an embodiment of the present disclosure.
Figure 3:
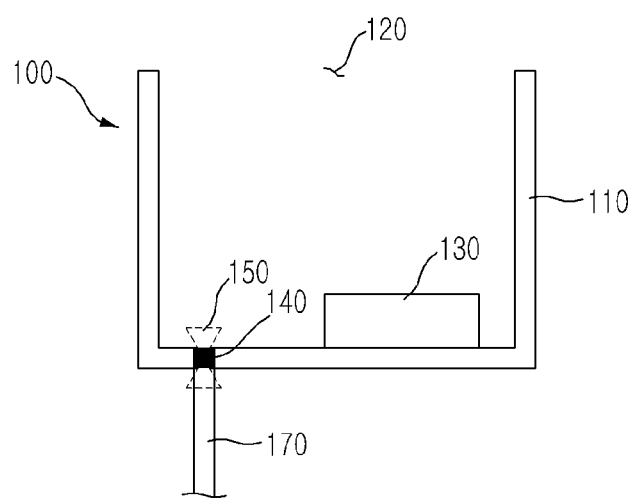
FIG. 3 is a disassembled view illustrating a humidification chamber and a drainage pipe provided at a humidifier in accordance with an embodiment of the present disclosure.

FIG. 1 is a view illustrating a humidifier in accordance with an embodiment of the present disclosure. FIG. 2 is a disassembled view illustrating a humidification chamber and a tray provided at a humidifier in accordance with an embodiment of the present disclosure. FIG. 3 is a disassembled view illustrating a humidification chamber and a drainage pipe provided at a humidifier in accordance with an embodiment of the present disclosure.

A humidifier in accordance with an embodiment of the present disclosure includes a humidification chamber 100, a storage chamber 200, an electrolytic unit 300, a fluid flow unit 400, a filter unit 500, and an operating unit 600.

The humidifier in accordance with an embodiment of the present disclosure, by restraining a proliferation of microorganism of a humidification chamber and a storage chamber using a principle of electrolytic sterilization of tab water, is capable of conducting a clean humidification.

The humidification chamber 100 is supplied with water from the storage chamber 200 and sprays the supplied water.

Such a humidification chamber 100 is provided with a first housing 110 forming an exterior thereof.

An opening 120 is formed at one side surface of the first housing 110, and an accommodation space is formed at an inside of the first housing 110.

That is, the water is atomized in the accommodation space of the humidification chamber 100, and the atomized water is sprayed through the opening 120.

A spray unit 130 is disposed at the accommodation space of the humidification chamber 100, and water is stored at an inside the accommodation space. Here, the spray unit 130 performs an atomization that atomizes water, and enables the atomized water to be spouted. In addition, the spray unit 130 is capable of evaporating water.

Such a spray unit 130 may be an apparatus capable of atomizing or evaporating the water at an inside the accommodation space.

As an non-limiting example, the spray unit 130 may be an ultrasonic type spray unit, a pressure spraying type spray unit, a heating type spray unit, a combination type spray unit having the heating type spray unit and the ultrasonic type spray unit integrated, a centrifugal spraying type spray unit, and a filter vaporization type spray unit.

The ultrasonic type spray unit includes a vibrator and a diaphragm. As for the principle of the ultrasonic type spray unit, the size of the vibrator is changed according to the frequency that corresponds to an alternating current, and the diaphragm which is in contact with the vibrator is vibrated according to the size change of the vibrator. According to the vibration of the diaphragm, ultrasonic waves are generated, and then the water is vibrated through the ultrasonic waves generated. At this time, the water is atomized, and the atomized water is spouted to an outside by the wind generated by the rotation of a fan.

The pressure spraying type spray unit is configured for the water to be discharged through a microscopic hole by pressurizing the water to reach a certain pressure level. At this time, the water discharged through the microscopic hole is naturally evaporated in the air.

The heating type spray unit is configured to generate steam by heating water using a heater or an electrode bar, and forcedly discharge the steam generated.

The combination type spray unit is configured for the water, after the water is heated, to be sprayed using ultrasonic waves.

The centrifugal spraying type spray unit is configured for water to be blown using centrifugal force to collide at a screen so that the water is atomized. At this time, the atomized water is emitted.

The filter vaporization type spray unit is configured to pass air through a wet filter for the water to be evaporated.

A drainage hole 140 is formed through a bottom portion of the first housing 110 of the humidification chamber 100.

The drainage hole 140 is configured for the water stored at the accommodation space at an inside the first housing 110 to be discharged to an outside.

The humidification chamber 100 further includes a drainage valve 150 configured to open or close the drainage hole 140.

The drainage valve 150, when the humidification mode or the sterilization mode is performed, by maintaining at an OFF state, enables the closed state of the drainage hole 140 to be maintained, hereby enabling the water to be accommodated at an inside the first housing 110.

The drainage valve 150, when the humidification mode or the sterilization mode are cancelled, enables the drainage hole 140 to be open by performing an ON operation, hereby enabling the water at an inside the first housing 110 to be discharged to an outside through the drainage hole 140.

Such a drainage valve 150 may be configured to be operated manually by a user. That is, opening/closing the drainage hole 140 manually may be possible.

A tray 160 is detachably coupled to a bottom surface of the humidification chamber 100.

The tray 160 is configured to store the water discharged through the drainage hole 140 of the first housing 110.

At this time, the water discharged through the drainage hole 140 is the water remaining after being used for the humidification or the water used for the sterilization.

That is, the tray 160 is detached from the humidification chamber 110 by a user, and at this time, a user may be able to throw away the water stored at the tray 160 that is detached from the humidification chamber 100.

As illustrated on FIG. 2, the tray 160 includes a second housing 161 forming an exterior thereof, a plurality of guide members 162 and 163 protrudedly formed from the second housing 161, and a handle member 164 formed at an outer side of the second housing 161.

Here, an accommodation space is formed at an inside the second housing 161. The accommodation space is configured to accommodate the water discharged from the first housing 110 of the humidification chamber 100.

The guide member 162 and the guide member 163 are positioned at an upper portion of the second housing 161, and the guide member 162 and the guide member 163 are disposed in a parallel to each other.

In addition, the guide member 162 and the guide member 163 are each disposed at a position corresponding to each of a plurality of guide grooves 111 and 112, respectively, formed at a bottom portion of the first housing 110 of the humidification chamber 100.

After the guide member 162 and the guide member 163 are inserted into the guide groove 111 and the guide groove 112, as the guide member 162 and the guide member 163 are moved along the guide groove 111 and the guide groove 112 in a sliding manner, the humidification chamber 100 and the tray 160 are mechanically coupled together. Although as a non-limiting example, only two guide members and two guide grooves are shown in FIG. 2, the present disclosure is not limited thereto. Any number of guide members may be positioned at an upper portion of the second housing 161 and the corresponding number of guide grooves may be formed at the bottom portion of the first housing 110. Further, at least one guide member may be formed at the bottom portion of the first housing 110 and the corresponding guide groove may be formed at the upper portion of the second housing 161.

The humidification chamber 100 and the tray 160 may be embodied in other detachable structure than the structure described herein.

The handle member 164 is configured for the tray 160 to be easily separated from the humidification chamber 100.

The tray 160 may further include a water level sensor (not shown) configured to measure the level of the water at an inside.

At this time, if the water level of the tray 160 exceeds a certain level, a user may be notified through a display unit that there is a need for the discard of waste water.

By further installing a pump (not shown) at the tray 160, delivering the water accommodated in the second housing 161 to the storage chamber 200 by pumping may be possible.

As illustrated on FIG. 3, the humidifier further includes a drainage pipe 170 installed at the drainage hole 140 of the humidification chamber 100.

The drainage pipe 170 is configured to guide the water discharged through the drainage hole 140 of the first housing 110 to an outside, hereby improving convenience of a user.

By further installing a pump (not shown) at the drainage pipe 170, guiding the water discharged through the drainage pipe 170 to the storage chamber 200 may be possible.

The storage chamber 200 is configured to store the water to perform a humidification of an indoor space or to sterilize the humidification chamber 100.

The water at the storage chamber 200 may be supplied by a user or directly supplied through an outside tap water pipe. At this time, the storage chamber 200 further includes a water supply pipe (not shown) and a water supply valve (not shown), and by opening/closing the water supply valve, controlling in the closing of the water supplied from an outside through the water supply pipe may be possible.

The storage chamber 200 includes a third housing 210 forming an exterior thereof and a cover 220.

An accommodation space is formed at an inside the third housing 210, and water is stored therein.

An opening is formed at one side surface of the third housing 210, and water is supplied to the third housing through the opening.

The storage chamber 200 includes the cover 220 configured to open/close the opening.

An electrolytic unit 300 is disposed at the accommodation space of the storage chamber 200.

The electrolytic unit 300 is configured to electrolyze the water stored at the storage chamber 200 at the humidification mode or the sterilization mode.

Here, the water may be tap water containing ion for the electrolysis may be possible. An electrolyte such as salt or hydrochloric acid may be dissolved in the water at the storage chamber 200 in order to activate electrolysis.

Such an electrolytic unit 300 includes a first electrode 310 and a second electrode 320, and the first electrode 310 and the second electrode 320 are connected to a power supply unit 630 and receive a voltage from the power supply unit 630.

When the voltage is applied to the first electrode 310 and the second electrode 320, current flows at the first electrode 310 and the second electrode 320 by the applied voltage. At this time, the first electrode 310 and the second electrode 320 each indicate a different polarity to each other.

For an example, as a positive (+) terminal of the power supply unit 630 is connected to the first electrode 310 and a negative (−) terminal of the power supply unit 630 is connected to the second electrode 320, the first electrode 310 indicates a positive polarity and the second electrode 320 indicates a negative polarity.

That is, by applying electricity having a negative polarity to the first electrode 310 and a positive polarity to the second electrode 320, the first electrode 310 may become a cathode and the second electrode 320 may become an anode. Alternatively, by applying electricity having a positive polarity to the first electrode 310 and a negative polarity to the second electrode 320, the first electrode 310 may become an anode and the second electrode 320 may become a cathode.

The lifespan of the first electrode 310 and the second electrode 320 as such may be extended by periodically changing the polarity of the first electrode 310 and the second electrode 320.

Here, the first electrode 310 and the second electrode 320 may be formed of a conductor including one selected from platinum (Pt), titanium (Ti), iridium (Ir), ruthenium (Ru), iron (Fe), aluminum (Al) and stainless (SS).

In addition, the first electrode 310 and the second electrode 320 may be formed of a conductor fused of at least two selected from platinum (Pt), titanium (Ti), iridium (Ir), ruthenium (Ru), iron (Fe), aluminum (Al) and stainless (SS).

The electrolytic unit 300 may also include one electrode.

When a direct current flows at the first electrode 310 and the second electrode 320 of the electrolytic unit 300, a positive ion moves toward the negative polarity electrode having a lower electric potential and a negative ion moves toward the positive polarity electrode having a higher electric potential. At this time, the electrical charge of the ion is neutralized at the surface of the first electrode 310 and the second electrode 320, and a chemical change is occurred.

In a case when the electrolysis is performed by using chloride ion (Cl⁻) present in tap water as an electrolyte, chlorine (Cl$_2$) is generated at the electrode having a positive (+) polarity and hydrogen is generated at the electrode having a negative (−) polarity. At this time, as the chlorine (Cl$_2$) generated is dissolved in the water, hydrogen chloride (HCl) is generated as well as hypochlorous acid (HClO) which is an effective component for sterilization The water at the storage chamber 200 is about at the level between pH 5.0 and pH 7.5, and the concentration of the remaining chlorine is about between 0.2 ppm and 3.0 ppm. The formula for the electrolysis at the first electrode 310 and the second electrode 320 is as below:

The formula for the electrolysis at the electrode having a positive (+) polarity is as follows:

$$2Cl^- \rightarrow Cl_2 + 2e^-$$

$$Cl_2 + H_2O \rightarrow HCl + HClO$$

In addition, water also may be electrolyzed at the electrode having positive (+) polarity, and the formula for such is as follows:

$$H_2O \rightarrow \tfrac{1}{2}O_2 + 2H^+ + 2e^-$$

The formula for the electrolysis at the electrode having a negative (−) polarity is as follows:

$$2H_2O + 2e^- \rightarrow H_2 + 2OH^-$$

Here, hydroxyl ion (OH⁻), by reacting with the hydrogen ion (H⁺) generated at the electrode having a positive (+)

polarity, generates water again, and the formula for such is as follows:

$$H^+ + OH^- \rightarrow H_2O$$

As such, through the electrolytic unit 300 at an inside the storage chamber 200, by electrolyzing the tap water at an inside the storage chamber 200, the hypochlorous acid component is generated. The hypochlorous acid component generated may flow through the fluid flow unit 400 while contained in the water.

That is, the water containing the hypochlorous acid component is stored at the storage chamber 200, and the water containing the hypochlorous acid component is supplied to the humidification chamber 100 at the humidification mode or the sterilization mode.

At this time, the storage chamber 200 supplies the water containing the hypochlorous acid component to the humidification chamber 100 through the fluid flow unit 400.

The fluid flow unit 400 controls the flow of the water from the storage chamber 200 to the humidification chamber 100.

The fluid flow unit 400 includes a first pipe 410 and a second pipe 420 connected between the first housing 110 of the humidification chamber 100 and the third housing 210 of the storage chamber 200, as well as a first valve 430 disposed at the first pipe 410 and configured to open/close a path of the first pipe 410 and a second valve 440 disposed at the second pipe 420 and configured to open/close a path of the second pipe 420.

A filter unit 500 is disposed at the first pipe 410. The filter unit 500 is configured to filter the water containing the hypochlorous acid component at the storage chamber 200.

Accordingly, the water supplied to the humidification chamber 100 through the first pipe 410 is the water obtained after the hypochlorous acid component is eliminated, and is used at the humidification mode. The water containing the hypochlorous acid component is supplied through the second pipe 420, and the sterilization of the humidification chamber 100 is performed by using such water during the sterilization mode.

The filter unit 500 includes a filter configured to eliminate the chlorine component, and the hypochlorous acid component, the filter implemented with a filter formed of components of activated carbon or the components of Zeolite. Such a filter unit 500 is provided in the form of at least one of a standing shape, a block shape, and a fabric shape.

The concentration of the chlorine and the number of germs in the water filtered through the activated carbon of the filter unit 500 are as follows:

TABLE 1

Concentration of Remaining Chlorine and Number of Germs in Water Filtered at Filter Unit

| Inlet Time (in minutes) | Concentration of Remaining Chlorine (ppm) | Number of Remaining Germs (CFU/ml) |
|---|---|---|
| 1 | 0.01 | <10 |
| 3 | 0.01 | <10 |
| 5 | 0.01 | <10 |

In addition, the sterilization rate in a case of using electrolyzed water is as follows:

TABLE 2

Sterilization Rate in accordance with Electrolysis of Electrolysis Unit

| Electrolysis Time (in minutes) | Concentration of Remaining Chlorine (ppm) | Number of Remaining Germs (CFU/ml) | Sterilization Rate (%) |
|---|---|---|---|
| 0 | 0.05 | 5.7 × 105 | — |
| 1 | 0.34 | <10 | 99.999 |
| 3 | 0.91 | <10 | 99.999 |
| 5 | 1.24 | <10 | 99.999 |

As such, it is understood that the chlorine component is eliminated from the water introduced to the humidification chamber 100 through the filter unit 500. That is, at the humidification, the hypochlorous acid component is removed through the filter unit, and thereby only the water component in a pure state having no germs is sprayed.

In addition, as the humidification chamber is sterilized by being supplied with the water containing the hypochlorous acid component, it is understood that no remaining germs are detected at an inside the humidification chamber. That is, it is understood that the proliferation of microorganisms may be restrained at an inside the humidification chamber.

Thus, a clean humidification having hazardous substance and bacterial contamination eliminated may be possible.

An input unit 610 includes a power ON/OFF button, and a mode selection button. Here, the mode includes the humidification mode and the sterilization mode.

The input unit 610 is configured to receive a command such as a humidification mode ON/OFF selection, and a sterilization mode ON/OFF selection.

A control unit 620 is configured to perform the humidification mode when the humidification mode ON is selected, cancels the humidification mode when the humidification mode OFF is selected, perform the sterilization mode when the sterilization mode ON is selected, and cancels the sterilization mode when a predetermined period of sterilization time elapses after the sterilization mode OFF is performed.

The control unit 620 may be capable of controlling the sterilization mode to be automatically performed when the humidification mode is cancelled. At this time, the entering of the sterilization mode is controlled to be performed after a predetermined period of time elapses.

The control unit 620, when the humidification mode or the sterilization mode is selected, by controlling the power supply unit 630, is configured to apply the voltage to the first electrode 310 and the second electrode 320 of the electrolytic unit 300, and hereby the electrolysis of the water is performed at an inside the storage chamber 200.

The control unit 620, by controlling the first valve 430 at ON position at the humidification mode, is configured to open the fluid path of the first pipe 410, and by controlling the second valve 440 at ON position at the sterilization mode, is configured to open the fluid path of the second pipe 420, and hereby water is supplied to the humidification chamber 100 through the first pipe 410 during the humidification mode and to the humidification chamber 100 through the second pipe 420 during the sterilization mode.

The control unit 620, when the humidification mode or the sterilization mode is cancelled, by controlling the drainage valve 150 at ON position, is configured to open the drainage hole 140, and hereby the water at an inside the humidification chamber 100 is discharged to an outside. Such will be explained by referring to FIG. 4.

FIGS. 4A-4E are a control view illustrating a case of a humidification mode and a sterilization mode of a humidifier in accordance with an embodiment of the present disclosure.

Figure 4A:
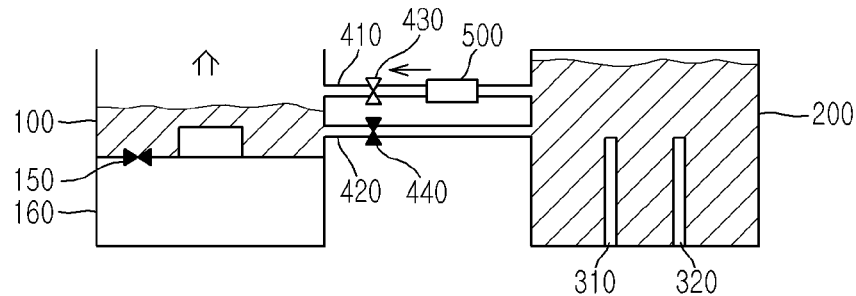
FIGS. 4A-4E are a view illustrating a control of a humidification mode and a sterilization mode of a humidifier in accordance with an embodiment of the present disclosure.

FIG. 4A shows the humidifier performing the humidification mode.

The control unit 620, when the humidification mode is selected, by controlling the power supply unit 630, is configured to supply the voltage to the first electrode 310 and the second electrode 320. At this time, the water at an inside the storage chamber 200 is electrolyzed, and the hypochlorous acid component is generated at this time.

The control unit 620 controls the first valve 430 to open and controls the second valve 440 and the drainage valve 150 to close, and hereby the humidification chamber 100 is supplied with the water of an inside the storage chamber 200 only through the first valve 430, and in addition, the water may be prevented from being discharged to an outside.

At this time, the water at an inside the humidification chamber 100 is the water supplied after being filtered through the filter unit 500, that is, the water having the hydrochloric acid eliminated.

The control unit 620 controls the operation of the spray unit 130 for the water to be sprayed. At this time, the spray unit 130 atomizes water, and emits the atomized water, and hereby the humidification of an indoor space is taken place.

The control unit 620, when the humidification mode is selected, by controlling the power supply unit 630 in order for the electrolysis to be prevented, may be capable of performing the humidification by using the water that is not electrolyzed.

At this time, since the hypochlorous acid component may be remained at an inside the storage chamber 200, controlling the first valve 430 may be possible for the water to be supplied through the first pipe 410 when the water is supplied from the storage chamber 200 to the humidification chamber 100.

Figure 4B:
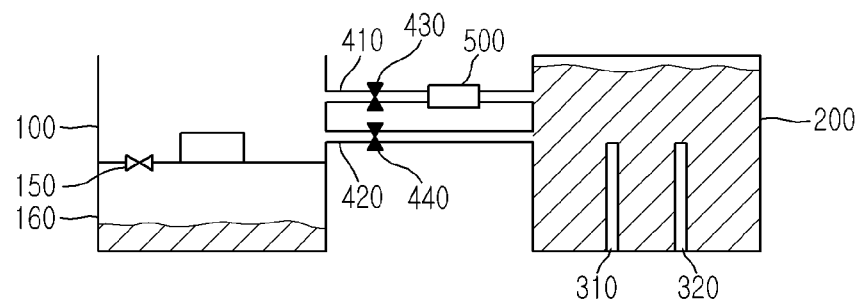

FIG. 4B shows the humidifier when the humidification mode is cancelled.

The control unit 620, when the humidification mode is cancelled, by controlling the first valve 430 at OFF position, is configured to close the fluid path of the first pipe 410, and in addition, is configured to control in the maintaining of the second valve 440 at OFF state in order for the water not to be supplied from the storage chamber 200 to the humidification chamber 100 through the second pipe 420.

The control unit 620, by controlling the drainage valve 150 at ON position, is configured to open the drainage hole 140. Thus, the water remaining at the humidification chamber 100, that is, the remaining water, is discharged to the tray 160 at an outside, and no water remains at the humidification chamber 100, and thereby no microorganisms may be proliferated so that the humidification chamber 100 may be managed in a clean state at all times.

The control unit 620, when a first predetermined period of drainage time elapses, is configured to control the drainage valve 150 at OFF position, thereby enabling the drainage hole 140 to be closed. Here, the first predetermined period of drainage time is the time consumed for the water at an inside the humidification chamber 100 to be entirely discharged to an outside.

Since a user may select the humidification mode again instantly after the humidification mode is cancelled, the drainage hole 140 may be controlled at ON position when a first predetermined period of time elapses.

Figure 4C:
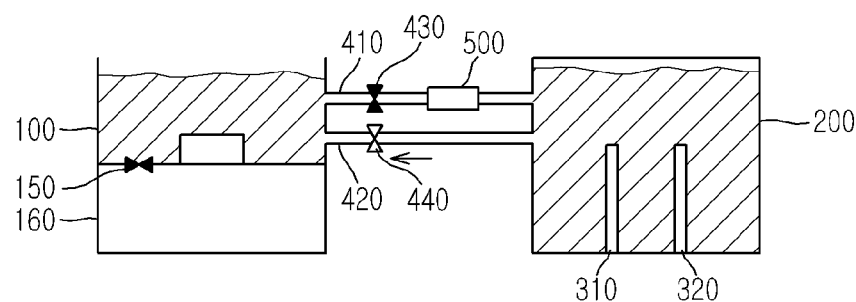

FIG. 4C shows the humidifier when the sterilization mode is performed.

The control unit 620, when the sterilization mode is selected through the input unit 610 or when a second predetermined period of time elapses after the humidification mode is cancelled, is configured to perform the sterilization mode.

At this time, the control unit 620, by controlling the power supply unit 630, is configured to supply the voltage to the first electrode 310 and the second electrode 320. Thus, the water at an inside the storage chamber 200 is electrolyzed, and the hypochlorous acid component is generated at this time.

The control unit 620 is configured to control the second valve 440 to open, and control the first valve 420 as well as the drainage valve 150 to close. Thus, the humidification chamber 100 is supplied with the water of the inside the storage chamber 200 only through the second valve 440, and the water supplied as such may be prevented from being discharged to an outside. At this time, the water at an inside the storage chamber 200 is the water containing hypochlorous acid.

The control unit 620 is configured to control the second valve 440 to open for a third predetermined period of time. Here, the third predetermined period of time is the time consumed for the water to be entirely filled at the humidification chamber 100, that is, the time when the amount of the water supplied through the second pipe 420 reaches below the capacity of the humidification chamber 100.

In addition, the third predetermined period of time is the time consumed for the amount of the water that is needed for the sterilization at the humidification chamber 100 to be supplied, and the third period of time may be attained through a test.

The control unit 620, when the third predetermined period of time elapses, is configured to control the second valve 440 to close and is configured to perform the sterilization of the humidification chamber 100 during a predetermined sterilization time. At this time, the humidification chamber 100 is sterilized by the water stored therein.

Here, the sterilization time is the time consumed for the microorganisms at an inside the humidification chamber 100 to be eliminated by the water stored at the humidification chamber 100, and is the time attained through a test.

Figure 4D:
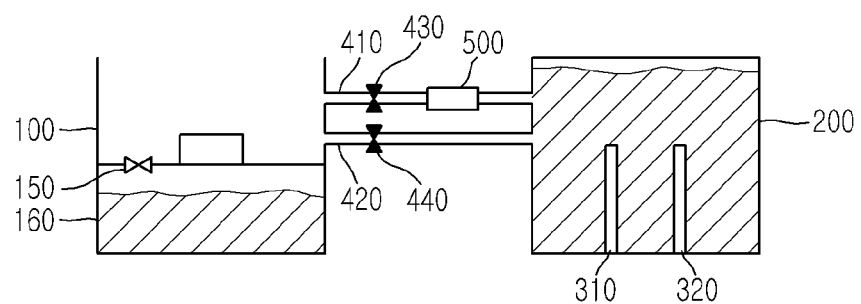

FIG. 4D shows the humidifier when the sterilization mode is cancelled.

The control unit 620, when the cancelling of the sterilization mode is selected or the sterilization time elapses, is configured to perform the cancelling of the sterilization mode.

At this time, the control unit 620, by controlling the first valve 430 and the second valve 440 at OFF position, is configured to entirely close each of the fluid paths of the first pipe 410 and the second pipe 420, and by controlling the drainage valve 150 at ON position, is configured to open the drainage hole 140. Through such, the water having been used for the sterilization is discharged to the tray 160 at an outside through the drainage hole 140.

The control unit 620, when a second predetermined period of drainage time elapses, controls the drainage valve 150 at OFF position so that the drainage hole 140 is closed. Here, the second predetermined period of drainage time is the time consumed for the water used for the sterilization at an inside the humidification chamber 100 to be entirely discharged to an outside.

Figure 4E:
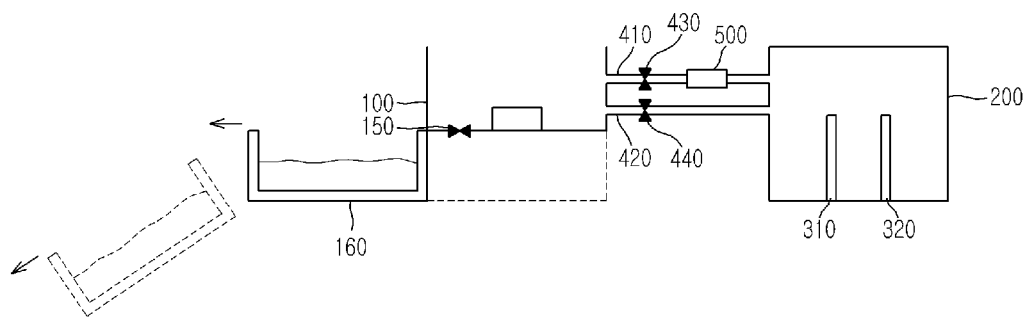

FIG. 4E shows the humidifier in a non-operation.

The control unit 620, in a state when the humidifier is not being used, that is, the state when the humidification mode or the sterilization mode are not being performed, by controlling the first valve 430 and the second valve 440 at OFF position, is configured to close each of the fluid path of the first pipe 410 and the second pipe 420, and is configured to close the drainage hole 140 by controlling the drainage valve 150 at OFF position.

A user detaches the tray 160 from the humidification chamber 100, throws away waste water of the tray 160, and couples again the tray 160 having the waste water eliminated to the humidification chamber 100.

Through such, the waste water of the tray 160 may be eliminated.

The power supply unit 630, following a command of the control unit 620, applies the voltage to the first electrode 310 and the second electrode 320.

A display unit 640 is configured to display a power ON/OFF, the amount of water at an inside the storage chamber 200, the amount of water at an inside the tray 160, and a selected mode according to a command of the control unit 620.

As described above, the humidifier is capable of eliminating the remaining water at the humidification chamber, preventing the contamination of the humidification chamber by having the sterilization water make contact with the humidification chamber at the time of the cancelling of the humidification mode, and preventing the chlorine element from being sprayed during the humidification mode by eliminating the sterilization water remaining at the humidification chamber during the humidification mode.

Figure 5:
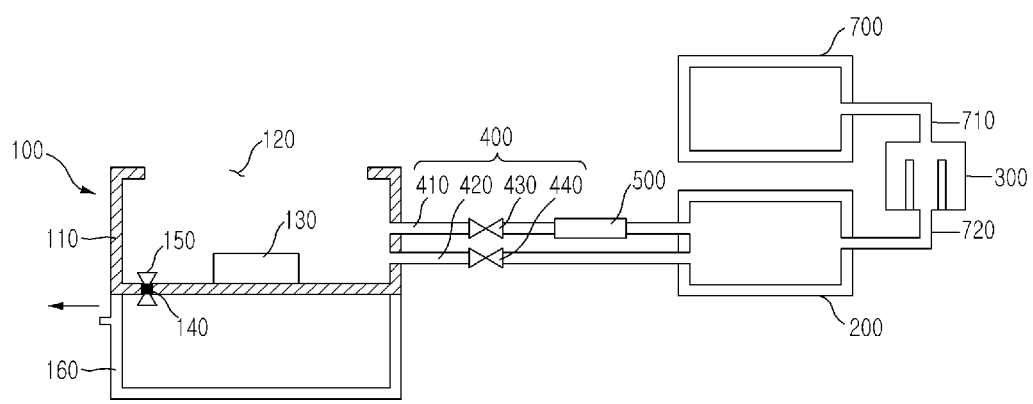
FIG. 5 is a view illustrating a humidifier in accordance with another embodiment of the present disclosure.
Figure 6:
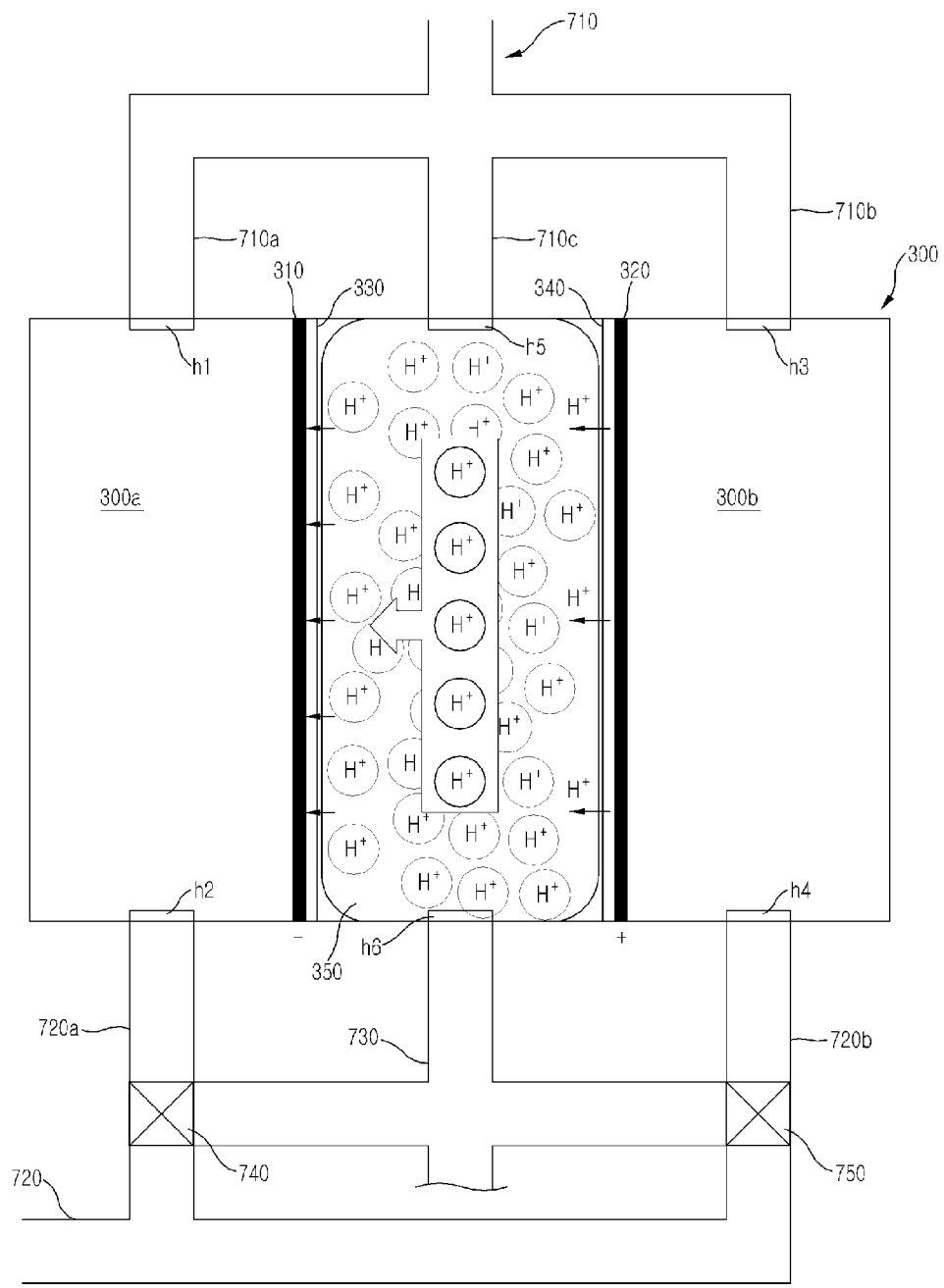
FIG. 6 is a view of an electrolytic unit provided at a humidifier in accordance with another embodiment of the present disclosure.
Figure 7A:
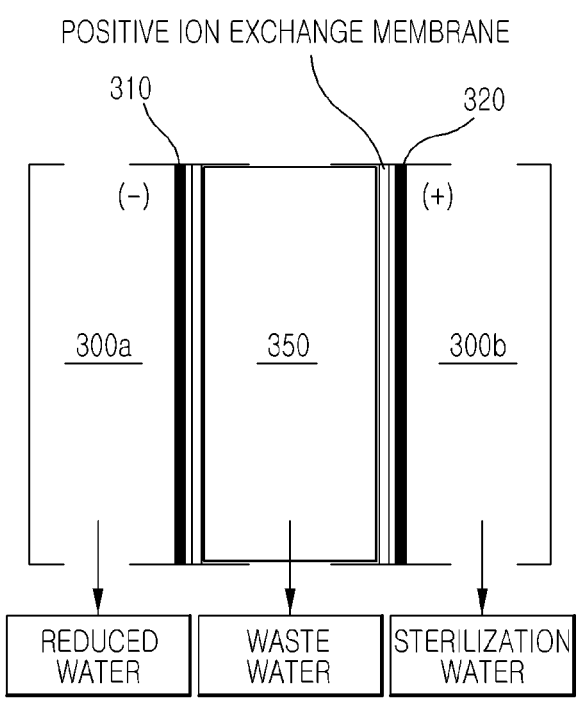
FIGS. 7A-7B area view illustrating the electrolysis of an electrolytic unit provided at a humidifier in accordance with another embodiment of the present disclosure.
Figure 7B:
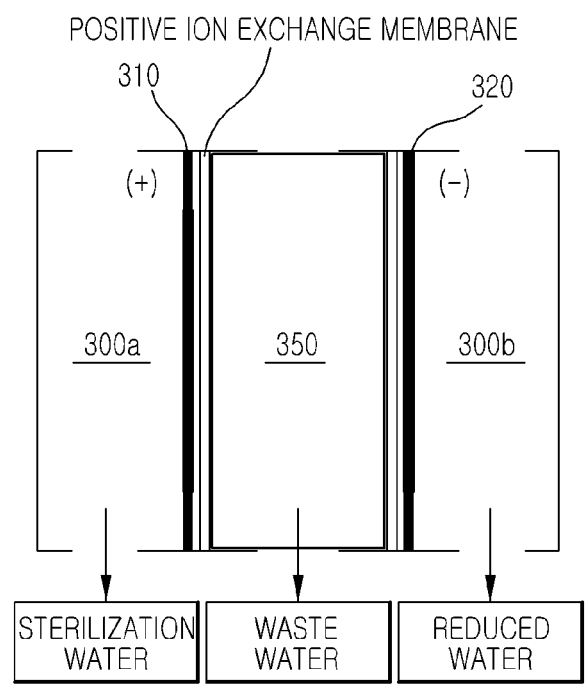

FIG. 5 is a view illustrating a humidifier in accordance with another embodiment of the present disclosure. FIG. 6 is a view of an electrolytic unit provided at a humidifier in accordance with another embodiment of the present disclosure. FIGS. 7A & 7B are a view illustrating the electrolysis of an electrolytic unit provided at a humidifier in accordance with another embodiment of the present disclosure.

In accordance with another embodiment of the present disclosure, a humidifier includes the humidification chamber 100, the storage chamber 200, the electrolysis unit 300, the fluid flow unit 400, the filter unit 500, the operating unit 600, and a water tank 700.

Here, the explanations of the humidification chamber 100, the fluid flow unit 400, the filter unit 500, and the operating unit 600 will be omitted, as such are same as those of the one embodiment of the present disclosure.

The storage chamber 200 is configured to store the electrolyzed water. Such storage chamber 200 is configured to store the electrolyzed water supplied from the electrolysis unit 300 disposed at an outside.

The electrolysis unit 300 receives water from the water tank 700, electrolyzes the water supplied, and supplies the electrolyzed water to the storage chamber 200. At this time, the electrolyzed water contains the hydrochloric acid element.

At this time, since the electrolysis unit 300 performs the electrolysis at an outside the storage chamber 200, and the electrolysis unit 300 electrolyzes a predetermined amount of water when needed and then supplies to the storage chamber 200, the electrolysis unit 300 may be able to supply the sterilization water having a predetermined level of sterilizing power to the storage chamber 200. Here the sterilization water refers to the water containing the hydrochloric acid component.

The electrolysis unit 300 is connected to the water tank 700 through a third pipe 710, and is connected to the storage chamber 200 through a fourth pipe 720. That is, the electrolysis unit 300 is supplied with water from the water tank 700 through the third pipe 710, and supplies the electrolyzed water to the storage chamber 200 through the fourth pipe 720.

The water tank 700 stores the water supplied by a user. In addition, the water tank 700 may be capable of storing the water by being supplied with the water from outside. In this case, the water tank 700 is provided with a water supply pipe (not shown) and a water supply valve (not shown) installed therein, and is capable of being supplied with the water from outside through the water supply pipe and the water supply valve.

The control unit 620, at the humidification mode, may be capable of performing the humidification by being supplied with the unelectrolyzed water from the water tank 700 in a state that the electrolysis of the electrolysis unit 300 is not performed through the electrolysis unit 300 and the storage chamber 200.

As illustrated on FIG. 5, the electrolysis unit 300 includes the first electrode 310 and the second electrode 320, and electrolyzes water by using the first electrode 310 and the second electrode 320.

As also illustrated on FIG. 6, the electrolysis unit 300 includes the first electrode 310, the second electrode 320, a first exchange membrane 330 and a second exchange membrane 340, and may be capable of performing the electrolysis by using the first electrode 310, the second electrode 320, the first exchange membrane 330 and the second exchange membrane 340. Here, the first exchange membrane 330 and the second exchange membrane 340 are the membranes having ion-permeability, and may be either positive ion exchange membranes or negative ion exchange membranes.

More particularly, the electrolysis unit 300 includes a first electrolytic chamber 300a and a second electrolytic chamber 300b having an electrolysis space at which the electrolysis is being generated, the first electrode 310 and the second electrode 320 disposed at the first electrolytic chamber 300a and the second electrolytic chamber 300b, respectively, while having a certain interval to each other, and the first exchange membrane 330 and the second exchange membrane 340 disposed between the first electrode 310 and the second electrode 320.

The electrolysis unit 300 may further include an ion exchange resin 350 disposed between the first exchange membrane 330 and the second exchange membrane 340.

The first electrolytic chamber 300a includes a first introduction hole (h1) through which the water is introduced and a first discharge hole (h2) through which the water is discharged, and the second electrolytic chamber 300b includes a second introduction hole (h3) through which the water is introduced and a second discharge hole (h4) through which the water is discharged. A third introduction hole (h5) is formed through one side surface of the ion exchange resin 350, and a third discharge hole (h6) is formed through an opposite side surface of the ion exchange resin 350.

The third pipe 710 through which the water is introduced is connected to the first introduction hole (h1), the second introduction hole (h3), and the third introduction hole (h5). At this time, a plurality of branch pipes 710a, 710b, and 710c which are branched out from the third pipe 710 are connected to the first introduction hole (h1), the second introduction hole (h3), and the third introduction hole (h5), respectively.

In addition, the fourth pipe 720 is connected to the first discharge hole (h2) and the second discharge hole (h4). At this time, a branch pipe 720a and a branch pipe 720b which are branched out from the fourth pipe 720 are connected to the first discharge hole (h2) and the second discharge hole (h4), respectively.

In addition, a waste water pipe 730 is connected to the third discharge hole (h6). The branch pipe 720a and the branch pipe 720b which are branched out from the fourth pipe 720 are connected to the waste water pipe 730.

A first switch valve 740 and a second switch valve 750 are disposed, respectively, at the branch pipe 720a which is connected to the first discharge hole (h2) and at the branch pipe 720b which is connected to the second discharge hole (h4).

The first switch valve 740 is disposed between the branch pipe 720a and the waste water pipe 730, and is configured to change the flow of the water which is electrolyzed at the first electrolytic chamber 300a. That is, the first switch valve 740 is configured in a way that the water electrolyzed at the first electrolytic chamber 300a is delivered to the storage chamber 200 or to the waste water pipe 730.

The second switch valve 750 is disposed between the branch pipe 720b and the waste water pipe 730, and is configured to change the flow of the water which is electrolyzed at the second electrolytic chamber 300b. That is, the second switch valve 750 is configured in a way that the water electrolyzed at the second electrolytic chamber 300b is delivered to the storage chamber 200 or to the waste water pipe 730.

The first switch valve 740, when an oxidation occurs at the first electrolytic chamber 300a, changes in a way that the water is supplied to the storage chamber 200, and when a reduction occurs at the first electrolytic chamber 300a, changes in a way that the water is supplied to the waste water pipe 730.

The second switch valve 750, when an oxidation occurs at the second electrolytics chamber 300b, changes in a way that the water is supplied to the storage chamber 200, and when a reduction occurs at the second electrolytic chamber 300b, changes in a way that the water is supplied to the waste water pipe 730.

That is, the control unit 620, based on the polarity of the electricity applied to the first electrode 310 and the second electrode 320, controls the opening direction of the first switch valve 740 and the second switch valve 750. Such will be explained by referring to FIG. 7. The embodiment of the present disclosure is explained in relation that the ion exchange resin 350 of is implemented with a positive ion exchange resin having a hydrogen ion ($H^+$) type as an example.

As illustrated on FIG. 7A, by applying a negative electricity to the first electrode 310 and a positive electricity to the second electrode 320, a reduction takes place at the first electrolytic chamber 300a and an oxidation takes place at the second electrolytic chamber 300b. At this time, the water flowing at the first electrolytic chamber 300a becomes reduced water and the water flowing at the second electrolytic chamber 300b becomes sterilization water containing the hypochlorous acid component. At this time, the second exchange membrane 340 serves as a positive ion exchange membrane.

The water emitted from the side of the first electrolytic chamber 300a is reduced water and the water emitted from the side of the ion exchange resin 350 is waste water, and the reduced water and the waste water are drained to an outside. The water emitted from the side of the second electrolytic chamber 300b is sterilization water, and the sterilization water is supplied to the storage chamber 200.

At this time, the first switch valve 740 is configured to be open toward the waste water pipe 730, and the second switch valve 750 is configured to be open toward the storage chamber 200.

As illustrated on FIG. 7B, by applying a positive electricity to the first electrode 310 and a negative electricity to the second electrode 320, an oxidation takes place at the first electrolytic chamber 300a and a reduction takes place at the second electrolytic chamber 300b. At this time, the water flowing at the first electrolytic chamber 300a becomes sterilization water containing the hypochlorous acid component and the water flowing at the second electrolytic chamber 300b becomes reduced water. At this time, the first exchange membrane 330 serves as a positive ion exchange membrane.

The water emitted from the side of the second electrolytic chamber 300b is reduced water and the water emitted from the side of the ion exchange resin 350 is waste water, and the reduced water and the waste water are drained to an outside. The water emitted from the second electrolytic chamber 300a is sterilization water, and the sterilization water is supplied to the storage chamber 200.

At this time, the first switch valve 740 is configured to be open toward the storage chamber 200, and the second switch valve 750 is configured to be open toward the waste water pipe 730.

As such, by changing the polarity of the first electrode 310 and the second electrode 320 such that the chambers at which the reduced water and the sterilization water are generated are exchanged to each other to reverse the flow of the water, the contamination of the first exchange membrane and the second exchange membrane may be prevented that occurs when the water flows to a single direction.

Figure 8:
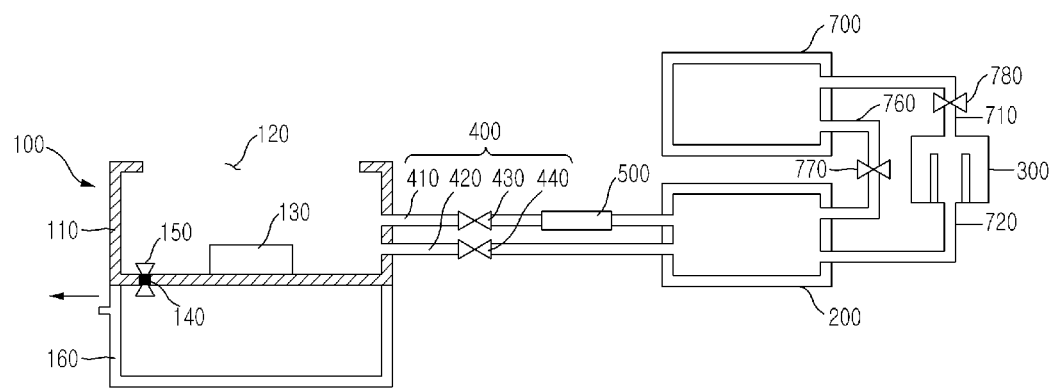
FIG. 8 is a view illustrating a humidifier in accordance with another embodiment of the present disclosure.

FIG. 8 is a view of a humidifier in accordance with another embodiment of the present disclosure.

In accordance with another embodiment of the present disclosure, a humidifier includes the humidification chamber 100, the storage chamber 200, the electrolysis unit 300, the fluid flow unit 400, the filter unit 500, the operating unit 600, and the water tank 700.

The humidifier includes a fifth pipe 760 configured to directly connect the storage chamber 200 to the water tank 700, a third valve 770 configured to open/close the path of the fifth pipe 760, and a fourth valve 780 configured to open/close the path of the third pipe 710.

Here, the explanations of the humidification chamber 100, the storage chamber 200, the electrolysis unit 300, the fluid flow unit 400, the filter unit 500, the operating unit 600, and the water tank 700 will be omitted, as such are same as those of the another embodiment of the present disclosure.

The control unit 620, at the humidification mode, by controlling the third valve 770 at ON position, enables the path of the fifth pipe 760 to be open. Through such, the storage chamber 200 is directly supplied with water from the water tank 700, and supplies the water to the storage chamber 200.

At this time, since the hydrochloric acid component may remain at the storage chamber 200, the control unit 620, by controlling the first valve 430, enables the path of the first pipe to be open, so that the water is supplied to the humidification chamber 100 through the filter unit 500.

The control unit 620, at the sterilization mode, by controlling the fourth valve 780 at ON position, enables the fluid path of each of the third pipe 710 and the fourth pipe 720 to be open, and controls the operation of the electrolysis unit 300.

Through such, the storage chamber 200 is supplied with the electrolyzed water from the electrolysis unit 300, and supplies the electrolyzed water to the storage chamber 200.

Figure 9:
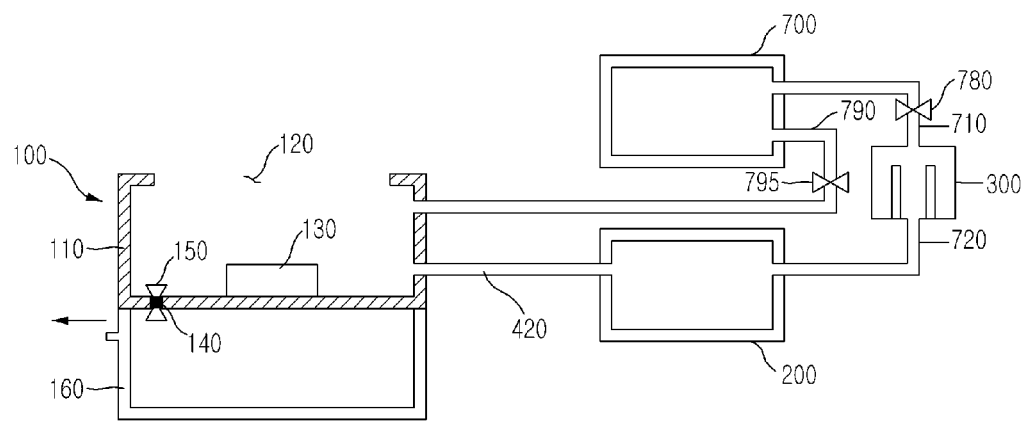
FIG. 9 is a view illustrating a humidifier in accordance with another embodiment of the present disclosure.

FIG. 9 is a view of a humidifier in accordance with another embodiment of the present disclosure.

In accordance with another embodiment of the present disclosure, a humidifier includes the humidification chamber 100, the storage chamber 200, the electrolysis unit 300, the fluid flow unit 400, the operating unit 600, and the water tank 700.

The humidifier includes the third pipe 710 configured to connect the electrolysis unit 300 to the water tank 700, the fourth valve 720 configured to connect the electrolysis unit 300 to the storage chamber 200, a sixth pipe 790 configured to directly connect the water tank 700 to the humidification chamber 100, a fifth valve 795 configured to open/close the path of the sixth pipe 790, and the fourth valve 780 configured to open/close the path of the third pipe 710.

Here, the explanations of the humidification chamber 100, the storage chamber 200, and the electrolysis unit 300 will be omitted, as such are same as those of the another embodiment of the present disclosure.

The fluid flow unit 400 only includes the second pipe 420 configured to the storage chamber 200 to the humidification chamber 100.

The control unit 620, during the humidification mode, by controlling the fifth valve 795 at ON position, enables the path of the sixth pipe 790 to be open, and controls the operation of the electrolysis unit 300. Through such, during the humidification mode, the humidification chamber 100 is directly supplied with water from the water tank 700, and sprays the water supplied, that is, tap water, from the water tank 700.

The control unit 620, during the sterilization mode, by controlling the fourth valve 780, enables the path of each of the third pipe 710 and the fourth pipe 720 to be open, and controls the operation of the electrolysis unit 300.

Through such, the storage chamber 200 is supplied with the electrolyzed water from the electrolysis unit 300, and supplies the electrolyzed water to the storage chamber 200 through the second pipe 420.

The humidification chamber 200 performs the sterilization by using the water supplied through the second pipe 420.

The control unit 620, in a case when the humidification mode or the sterilization mode is cancelled, controls the drainage valve 150 at ON position for the water having been used for the humidification and the sterilization is discharged, thereby preventing the water from remaining at the humidification chamber 100.

As such, the sterilization of the humidification chamber may be possible by using the electrolyzed water, and, the water remaining at the humidification chamber may be eliminated by discharging the remaining water to an outside, thereby preventing the proliferation of microorganisms.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. A humidifier, comprising:
   a storage chamber configured to store water;
   an electrolytic unit configured to electrolyze water at the storage chamber;
   a first pipe and a second pipe to which the electrolyzed water is introduced;
   a first valve configured to open/close a fluid path of the first pipe;
   a second valve configured to open/close a fluid path of the second pipe;
   a filter unit disposed at the first pipe and configured to filter the electrolyzed water;
   a humidification chamber configured to be supplied with water from one of the first pipe or the second pipe, the humidification chamber comprising a drainage hole configured to discharge water and a drainage valve configured to open/close the drainage hole;
   a tray installed at the humidification chamber and configured to store the water discharged through the drainage hole of the humidification chamber; and
   a control unit configured to supply the filtered water to the humidification chamber at a humidification mode by controlling the first valve, to discharge a remaining of the filtered water that remains after being used for a humidification to the tray though the discharge hole by controlling the drainage valve at an ON position when the humidification mode is cancelled, to supply the electrolyzed water to the humidification chamber at a sterilization mode by controlling the second valve when the discharge is completed, and to discharge the sterilized water to the tray by controlling the drainage valve at the ON position when the sterilization mode is cancelled,
   wherein the electrolyzed water at the humidification mode is a part of the water electrolyzed by the electrolytic unit, and the electrolyzed water at the sterilization mode is the remaining of the water electrolyzed by the electrolytic unit.

2. The humidifier of claim 1, wherein the humidification chamber further comprises:
   a spray unit configured to spray the filtered water at the humidification mode.

3. The humidifier of claim 1, further comprising a drainage pipe connected to the drainage hole and configured to discharge the water of the humidification chamber to be discharged to an outside.

4. The humidifier of claim 1, wherein the electrolytic unit is disposed at an inside of the storage chamber.

5. The humidifier of claim 1, wherein the electrolytic unit comprises a first electrode and a second electrode.

6. The humidifier of claim 5 wherein the electrolytic unit comprises a first electrolytic chamber having the first electrode disposed thereon, a second electrolytic chamber having the second electrode disposed thereon, and an exchange membrane disposed between the first electrolytic chamber and the second electrolytic chamber, the electrolytic unit configured to discharge reduced water between the reduced water and sterilization water that are generated at the first electrolytic chamber and the second electrolytic chamber to the outside while supplying the sterilization water to the storage chamber.

7. The humidifier of claim 1, further comprising:
   a water tank configured to supply water to the storage chamber,
   wherein the electrolytic unit is configured to electrolyze water supplied from the water tank and to deliver the electrolyzed water to the storage chamber.

8. The humidifier of claim 7, wherein the electrolytic unit further comprises:
a third pipe connected to the water tank; and
a fourth pipe configured to guide the sterilization water to the storage chamber.

9. The humidifier of claim 1, wherein the filter unit comprises one of activated carbon and Zeolite.

10. The humidifier of claim 9, wherein the filter unit is provided in a form of a standing shape, a block shape, or a fabric shape.

11. The humidifier of claim 1, wherein the tray is detached/attached from the humidification chamber.

12. The humidifier of claim 1, wherein the tray includes at least one guide member formed at an upper portion of the tray, and the humidification chamber includes at least one guide groove formed at a bottom portion of the humidification chamber and corresponding to the at least one guide member, so that the at least one guide member and the at least one guide groove are coupled together by a sliding manner.

13. The humidifier of claim 1, wherein the humidification chamber includes at least one guide member formed at a bottom portion of the humidification chamber and the tray includes at least one guide groove formed at an upper portion of the tray and corresponding to the at least one guide member, so that the at least one guide member and the at least one guide groove are coupled by a sliding manner.

14. The humidifier of claim 1, wherein the filter unit is configured to eliminate a chlorine component and/or a hypochlorous acid component of the electrolyzed water.

15. A humidifier, comprising:
a humidification chamber having a spray unit configured to spray water;
a storage chamber configured to supply water to the humidification chamber;
an electrolytic unit configured to electrolyze the water of the storage chamber;
a first pipe and a second pipe to which the electrolyzed water is introduced;
a first valve configured to open/close a fluid path of the first pipe;
a second valve configured to open/close a fluid path of the second pipe;
a filter unit disposed at the first pipe and configured to filter the electrolyzed water;
a control unit configured to supply the filtered water to the humidification chamber at a humidification mode by controlling the first valve, to control an operation of the spray unit at the humidification mode, and to supply the electrolyzed water to the humidification chamber at a sterilization mode by controlling the second valve,
wherein the electrolyzed water at the humidification mode is a part of the water electrolyzed by the electrolytic unit, and the electrolyzed water at the sterilization mode is the remaining of the water electrolyzed by the electrolytic unit.

16. The humidifier of claim 15, further comprising:
a tray installed at the humidification chamber and configured to store water discharged through the humidification chamber,
wherein
the humidification chamber further includes a drainage hole configured to discharge water, and a drainage valve configured to open/close the drainage hole, and
the control unit is configured to control the drainage valve at an ON position when the humidification mode is cancelled, and to control the drainage valve at the ON position when the sterilization mode is cancelled.

17. The humidifier of claim 16, wherein the control unit is configured to control the drainage valve at the ON position when a first predetermined period of time elapses after the humidification mode is cancelled.

18. The humidifier of claim 17, wherein the control unit is configured to control the drainage valve at an OFF position when a second predetermined period of time elapses after the humidification mode is cancelled, and to supply the electrolyzed water to the humidification chamber through the second pipe by controlling the second valve at an ON position.

19. The humidifier of claim 18, wherein the control unit is configured to control the second valve at an OFF position when a third predetermined period of time elapses after the second valve is at the ON position, and to control an execution of the sterilization mode during a predetermined period of sterilization time.

20. The humidifier of claim 19, wherein the control unit is configured to open the drainage hole by controlling the drainage valve at the ON position when the sterilization time elapses.

21. The humidifier of claim 16, wherein the drainage valve is operated manually.

22. The humidifier of claim 15, wherein the electrolytic unit comprises a first electrolytic chamber having a first electrode disposed thereon, a second electrolytic chamber having a second electrode disposed thereon, and an exchange membrane disposed between the first electrolytic chamber and the second electrolytic chamber, the electrolytic unit configured to supply water containing hypochlorous acid generated from one of the first electrolytic chamber and the second electrolytic chamber to the storage chamber.

23. The humidifier of claim 22, further comprising a power supply unit configured to apply a voltage to the first electrode and the second electrode provided at the electrolytic unit at the humidification mode and the sterilization mode.

24. The humidifier of claim 15, wherein the electrolytic unit comprises a first electrode and a second electrode, and the first electrode and the second electrode are positioned at an inside of the storage chamber.

* * * * *